United States Patent
Gao et al.

(10) Patent No.: US 12,397,158 B2
(45) Date of Patent: Aug. 26, 2025

(54) SYSTEM FOR LOCALLY ACTIVATING THE HUMAN EYE AND THE BRAIN IN ORDER TO TRAIN VISUAL PERFORMANCE, IN PARTICULAR IN ORDER TO ACTIVATE THE VISUAL CORTEX AND REORGANIZED NEURAL NETWORKS IN THE HUMAN BRAIN IN ORDER TO STRENGTHEN RESIDUAL VISION

(71) Applicant: SAVIR GMBH, Berlin (DE)

(72) Inventors: Ying Gao, Magdeburg (DE); Kornelia Sabel, Berlin (DE)

(73) Assignee: SAVIR GMBH, Berlin (DE)

( * ) Notice: Subject to any disclaimer, the term of this patent is extended or adjusted under 35 U.S.C. 154(b) by 282 days.

(21) Appl. No.: 17/753,374

(22) PCT Filed: Sep. 2, 2020

(86) PCT No.: PCT/EP2020/074408
§ 371 (c)(1),
(2) Date: Mar. 1, 2022

(87) PCT Pub. No.: WO2021/052754
PCT Pub. Date: Mar. 25, 2021

(65) Prior Publication Data
US 2022/0314000 A1    Oct. 6, 2022

(30) Foreign Application Priority Data

Sep. 20, 2019 (DE) .......................... 102019125416.7
Sep. 27, 2019 (DE) .......................... 102019126163.5
(Continued)

(51) Int. Cl.
*A61N 1/36* (2006.01)
*A61N 1/04* (2006.01)

(52) U.S. Cl.
CPC ....... *A61N 1/36046* (2013.01); *A61N 1/0456* (2013.01); *A61N 1/0472* (2013.01); *A61N 1/36031* (2017.08)

(58) Field of Classification Search
CPC .............. A61N 1/36046; A61N 1/0456; A61N 1/0472; A61N 1/36031
See application file for complete search history.

(56) References Cited

U.S. PATENT DOCUMENTS 5,522,864 A    6/1996  Wallace et al. ................. 607/53
9,566,427 B2   2/2017  Wagner
(Continued)

FOREIGN PATENT DOCUMENTS

CN         1065392 A      10/1992   ............... A61F 9/00
CN       109045435 A   *  12/2018   ............. A61N 1/046
(Continued)

OTHER PUBLICATIONS

Gall, et al., "*Alternating Current Stimulation for Vision Restoration after Optic Nerve Damage: A Randomized Clinical Trial*", PLoS One, vol. 11, No. 6, Jun. 29, 2016, the whole document. Abstract and full text available at: https://journals.plos.org/plosone/article?id=10.1371/journal.pone.0156134 (last accessed on May 25, 2022).
(Continued)

*Primary Examiner* — Carl H Layno
*Assistant Examiner* — Maria Catherine Anthony
(74) *Attorney, Agent, or Firm* — Bodner & Bodner, PLLC; Christian P. Bodner; Gerald T. Bodner

(57) ABSTRACT

The invention relates to a system for locally activating the nervous system in the human eye and in the brain by means of a non-invasive pulse treatment in order to strengthen residual vision in cases of existing visual field defects, consisting of an applicator for guiding a flow of current to the eye and/or brain and to excite the circulation and activate
(Continued)

nerve cells, in particular nerve cells of the visual system and retinal ganglion cells, a pulse generator for generating electric stimulation signals, and a data processing and control unit for providing patient-specific stimulation signal sequences, wherein the applicator has at least two electrodes which can be brought into contact with the head of the subject. Replaceable stimulation electrodes are fixed to the applicator such that the electrodes rest to the right and to the left of the eye in the region of the temple of the patient's head. The applicator additionally has at least one assembly for non-invasively determining the circulation of the skin and the brain and for determining the oxygen saturation in order to improve the stimulation effect in this regard when using the system.

23 Claims, 2 Drawing Sheets

(30) Foreign Application Priority Data

| Oct. 9, 2019 | (DE) | ......................... 102019127098.7 |
| Nov. 11, 2019 | (DE) | ......................... 102019130302.8 |

(56) References Cited

U.S. PATENT DOCUMENTS

| 10,391,312 B2 | 8/2019 | Mowery et al. | |
| 2006/0129207 A1 | 6/2006 | Fried et al. | ..................... 607/54 |

FOREIGN PATENT DOCUMENTS

| DE | 102011055844 B4 | 1/2014 | ............... A61F 9/00 |
| EP | 1332771 A2 * | 8/2003 | ............ A61N 1/046 |
| EP | 1708787 B1 | 6/2011 | ............. A61G 15/12 |
| EP | 1603633 B1 | 8/2012 | ............... A61N 1/00 |
| EP | 2651504 B1 | 12/2014 | ............... A61N 1/04 |
| EP | 1734877 B1 | 10/2015 | ............. A61B 17/52 |
| EP | 2981326 B1 | 5/2018 | ............... A61B 5/00 |
| EP | 3349844 A1 | 7/2018 | ............... A61N 1/04 |
| EP | 3013414 B1 | 9/2018 | ............... A61N 1/04 |
| EP | 3598962 A1 | 1/2020 | ............... A61H 5/00 |
| EP | 3349844 B1 | 1/2021 | ............... A61N 1/04 |
| JP | H0975465 A | 3/1997 | ............... A61N 1/32 |
| WO | WO2011106660 A1 | 9/2011 | ............... A61N 1/36 |
| WO | WO2013037618 A1 | 3/2013 | ............... A61N 1/36 |
| WO | WO2014141213 A1 | 9/2014 | ............... A61F 5/34 |
| WO | WO2016115392 A1 | 7/2016 | ............... A61N 1/00 |
| WO | WO2017048731 A1 | 3/2017 | ............... A61N 1/04 |
| WO | WO-2017222997 A1 * | 12/2017 | ............... A61B 3/09 |

OTHER PUBLICATIONS

The Notification Concerning Transmittal of International Preliminary Report on Patentability (Chapter I of the Patent Cooperation Treaty), in English, dated Mar. 31, 2022, which was issued by the International Bureau of WIPO in Applicant's corresponding international PCT application having Serial No. PCT/EP2020/074408, filed on Sep. 2, 2020.

The English translation of the International Preliminary Report on Patentability (Chapter I of the Patent Cooperation Treaty), dated Mar. 15, 2022, which was issued by the International Bureau of WIPO in Applicant's corresponding international PCT application having Serial No. PCT/EP2020/074408, filed on Sep. 2, 2020.

The Written Opinion of the International Searching Authority, in English, dated Nov. 26, 2020, which was issued by the International Bureau of WIPO in Applicant's corresponding international PCT application having Serial No. PCT/EP2020/074408, filed on Sep. 2, 2020.

The International Search Report, in English, dated Nov. 26, 2020, which was issued by the International Bureau of WIPO in Applicant's corresponding international PCT application having Serial No. PCT/EP2020/074408, filed on Sep. 2, 2020.

An Office Action (in German), dated Jul. 15, 2020, issued by the German Patent Office for Applicant's corresponding German Patent Application No. DE102019130302.8, filed Nov. 11, 2019.

* cited by examiner

SYSTEM FOR LOCALLY ACTIVATING THE HUMAN EYE AND THE BRAIN IN ORDER TO TRAIN VISUAL PERFORMANCE, IN PARTICULAR IN ORDER TO ACTIVATE THE VISUAL CORTEX AND REORGANIZED NEURAL NETWORKS IN THE HUMAN BRAIN IN ORDER TO STRENGTHEN RESIDUAL VISION

BACKGROUND OF THE INVENTION

The invention relates to a system for locally activating the human eye and the brain in order to train visual performance, in particular for activating nerve cells in the human eye and brain by means of a non-invasive pulse treatment, in particular alternating current pulse treatment (tASC), in order to strengthen residual vision in cases of visual field defects, consisting of an applicator for guiding a flow of current to the eye and/or brain and to excite the circulation and activate nerve cells of the visual system, in particular retinal ganglion cells, a pulse generator for generating electric stimulation signals, and a data processing and control unit for providing patient-specific stimulation signal sequences, wherein the applicator has at least two electrodes which can be brought into contact with the head of the subject, according to the preamble of claim 1.

Visual field defects are hitherto considered to be irreversible, since nerve cells of the retina, of the nervus opticus and the brain are not able to regenerate. It has shown, however, that a partial recovery from visual field defects is possible since the brain, which evaluates and interprets retinal signals is able to permanently enhance the residual signals via certain mechanisms. In the retina there are also nerve cells which reduce their function after a pathological event and "become mute" since they are no longer able to emit nerve signals, yet without really passing away.

Since experience shows that in almost all patients, residual vision performance, i.e. residual viewing, is still existent, it has been proposed to perform a reactivation of the "mute" nerve cells and to strengthen the residual vision performances via the improvement of synaptic transmission. Clinical studies show the success of treatment methods of visual training or alternating current stimulation. During the alternating current treatment, the entire retina and parts of the brain are activated and synchronized. A vast majority of the patients has a good response to the therapy forms mentioned above. Physiological examinations of the mechanisms of alternating current using EEG and fMRT indicate a massive and global change of circulation and re-organization of neural networks in the brain. A local activation of the nerve cells takes place in the eyes and the visual system of the brain via a global re-organization of neural networks. Since residual viewing can be strengthened via re-activating nerve cells and modulating neuroplasticity, not only the eyes but also the brain is largely important for the visual rehabilitation in ophthalmology.

For some time, the brain's adaptability, also called plasticity, has been utilized for ophthalmology. Via methods of neuromodulating by means of weak alternating currents, partially damaged visual functions can be strengthened due to the process of neuroplasticity.

More recently, methods for blood circulation enhancement and re-synchronization of the network activity of the brain by means of alternating current pulses have been tested and examined on patients that have become partially blind. On this occasion, alternating current is administered non-invasively for several days in defined sessions by means of special electrodes on the forehead. The alternating current flows in this case from the electrodes to the eye and excites retinal ganglion cells there to fire in predetermined frequencies with the objective of re-synchronizing brain networks. A damage of the nervus opticus namely results in a disorganization of functional networks in the brain, which becomes noticeable by a neurophysiological desynchronization in the EEG. Treatments by means of alternating current can significantly improve this state via blood circulation enhancement and re-synchronization of brain network activity.

The re-synchronization of visual performance, however, is very different from person to person and depends on a vast variety of different factors.

Apart from optimizing the stimulation pulses, it is also important in this case for the patient to be largely kept free from stress at least during treatment. For this purpose, there is the necessity of creating an optimized formation of stimulation electrodes including technical means for mounting these electrodes on the patient's head. Consequently, an applicator needs to be created which is both ergonomically optimal and, as far as treatment technology is concerned, is particularly suitable and fulfills all requirements.

Furthermore, it is essential for configuring an optimization of the stimulation such that a treatment success is maintained even beyond the stimulation time and as long as possible.

As to the state of the art, reference is made to EP 1 603 633 B1 with respect to the aspects mentioned above, which shows a special fastening part for a stimulation device on a desired position on the patient's head, wherein an adjustment structure is made of a deformable material, which is capable of adapting the device to contours of the patient's head.

Fastening devices or arrangements for positioning stimulation electrodes in a contacting manner are furthermore disclosed in EP 1 708 787 and EP 1 734 877 B1.

With regard to the state of the art with respect to brain stimulation by means of additionally controlling the blood circulation behavior of adjacent vessels, attention should be drawn to WO 2011/106660 A1 and WO 2016/115392 A1.

In the document WO 2011/106660 A1, reference is made to recognizing the effect of a stimulation and in particular the simultaneous stimulating and detecting of the stimulation effect in real-time. During stimulation, a functional near infrared spectroscopy is utilized in a non-invasive manner for this purpose. In this case, the functional near infrared spectroscopy is used so as to measure the oxygen generation state of hemoglobin.

The document WO 2016/115392 A1 relates to devices and methods for determining the neurovascular reactivity while using a stimulation of the neurovascular system and simultaneously recording a neural hemodynamic response to it.

With regard to the various possibilities of forming stimulation electrodes and corresponding applicators, attention should be drawn to the state of the art briefly outlined below.

The document U.S. Pat. No. 5,522,864 A discloses a headband-like electrode fixation. A first electrode is placed on the closed eyelid of a patient. The second electrode is fixed in the headband. A third electrode is placed in the neck region. Such an electrode formation, in particular placing an electrode on a closed eyelid, is experienced by the patient as being unpleasant and shifts him into a stress that is negative to the treatment success.

Also, in the patent family around EP 30 13 414 B1, which shows a stimulation device for transdermal electric stimulation, several electrodes are fixed at positions which are significantly spaced from one another. A first electrode is fixed to the patient's forehead region. A second electrode is located on the neck or the shoulder of the patient. This electrode arrangement is difficult to be adapted from person to person and may only be positioned optimally by the patient with the help of third parties, which represents a considerable disadvantage for home therapy.

In the document EP 33 49 844 A1, the matter is treatment by applying microcurrents. In this respect, punctual stimulation electrodes are placed above and below the eye in the lid region. Such a positioning immediately in the sensitive eye region is unpleasant for a great number of patients, in particular also because the electrodes are relatively small and thus do not enable sufficient current strength. Already very low currents are perceptible which, however, are not sufficiently therapeutically affective. It is just in the region above and below the eye, where human skin is very sensitive to irritations, so that such an electrode formation did not find any appreciable distribution.

The document EP 2 981 326 B1 shows a head set-like arrangement for electrically stimulating the skin surface of the head.

The document DE 10 2011 055 844 B4 discloses a spectacles-like carrier for stimulation electrodes, wherein a nose support is present in addition similar to typical spectacles. The electrodes there are designed to be removable, i.e. exchangeable. However, hair electrodes are employed in this arrangement, which lie directly on the cornea of the eyeball, which leads to risks of damaging the cornea.

The document EP 2 651 504 B1 provides a headband as an electrode carrier for neurostimulation, wherein the headband makes contact in the patient's head region, and corresponding electrodes make symmetrically contact at the patient's back of the head. Furthermore, electric terminals for connecting the electrodes with a separate pulse generator are present.

The device according to US 2006/129207 A in turn takes a spectacles-like structure as a basis for electrically stimulating ganglion cells, which structure has electrodes which are associated with the person's lid. The otherwise unpleasant pressure acting upon the eyelids is intended to be minimized via a support, which, however, results in the disadvantage that a size of the contact resistance between the electrodes and the person's skin cannot always be reproduced unambiguously.

In summary, the state of the art shows a great number of different applicators for electric stimulation also for the case that is relevant here of locally activating the eyes and the brain, wherein the plurality of known applicators is not suitable for home therapy, i.e. in terms of a reproducible, simple and risk-free application by the patient without medical or surgical support.

For this reason—and ultimately also from cost considerations—reference is made at present largely preponderantly to large-scale adhesive stimulation electrodes which are fixed to the respective person or patient according to experience values of the medical personnel. The advantage of larger electrodes is that a sufficient current intensity may be administered since the flow of current penetrates into the skin, the eyes or the cranium via a larger surface. In this respect, a trial-and-error method is frequently used with the consequence of an only very restricted reproducibility. Given the basis of adhesive electrodes, home applications are also almost excluded so that, basically, an ambulant preparation of the therapy is required.

The state of the art consequently reports very different electrode sizes and positionings, which, however, are very variable in their effects and thus not sufficiently reproducible. For this reason, it is desirable to enable a suitable electrode placement which is able of modulating the visual system even at lower currents and even at a lower variability.

SUMMARY OF THE INVENTION

From the aforementioned, it is a task of the invention to carry out an individual electrode adaptation by means of the patient-specific physical preconditions. For this purpose, a novel system is intended to be created, which, on the one hand, generates an optimum arrangement of the stimulation electrodes, and which ensures a persistent effect after and not only during the stimulation treatment.

The solution of the task of the invention is performed with a system according to the feature combination of claim 1 and a special application according to the teaching of claim 18 or 19, wherein the subclaims comprise at least appropriate configurations and further developments.

In this case, it is an essential aspect of the invention to permit the application of the applicator to be intuitive, wherein, via an assembly for non-invasively determining the blood circulation of the person's skin and brain and for determining the oxygen saturation, an optimum stimulation sequence can be found, which leads to a maximum blood circulation increase and to a longest persisting after-effect such that the blood flow increase and neural activation continues as long as possible even after the stimulation, which is a clear indicator for the aspired treatment success.

The pulse generator for generating the stimulation signal sequences may be a one-channel stimulator or a multichannel stimulator cooperating with a data processing and control unit so that patient-specific stimulation signal sequences are generated.

The temple positioning according to the invention makes it possible to stimulate both eyes at the same time by only one channel which reduces the costs of manufacturing the stimulation generator and improves the effectiveness and reliability, i.e. a lower variability of the success.

The optimum stimulation signal sequences can be detected at a first treatment under medical supervision, can then be stored and delivered to the patient on a patient memory card for home application. It is likewise possible to carry out data storage directly in a memory unit of the applicator.

According to the invention, the applicator is built such that an intuitive use may take place after a short explanation of the handling, in particular also in the home region.

Since it has been shown that a treatment success occurs in particular when the patient is kept free from stress immediately before but also during the treatment, the applicator in an embodiment of the invention disposes of sound generating means which are in particular formed as earphones or headphones. Via these sound generating means, the patient may be taught on the one hand how to operate the applicator, which program is to be selected, how long the treatment duration continues or the like. Furthermore, playing in of voice messages, tone sequences or music my also take place for the purpose of a desired relaxation response.

The applicator according to the invention thus comprises an electrode holder which is in particular individually adaptable to the head shape. Furthermore, temple positioning of the electrodes is performed for an optimum stimulation. This results in the advantage that the current intensity of the pulse sequences may be reduced and nevertheless sufficient phosphenes are generated. Over a NIR feedback system, a maximization of the hemodynamic after-effect may be created in the non-invasive eye and brain stimulation.

In the course of extensive examinations and studies made by the Applicant, it has been shown that the arrangement of the electrodes plays a decisive role for the stimulation success of the visual system.

In this respect, according to the invention, a so-called F7-F8 arrangement according to the nomenclature of the system EEG 10-20 in the region of the patient's temples is proposed. In such an arrangement, phosphenes are registered in fact with extremely low current intensities in the range of less than 2 mA at an alternating current frequency in the range of 8 to 25 Hz. If electrodes are positioned in the F7-F8 region, the patient may close the exes or keep them open in a dark room. An unpleasant pressure in the region of the lid or above or below the eye due to placed or applied electrodes does not occur.

If wet electrodes are utilized and arranged in the region F7-F8, a very pleasant cooling effect occurs further which results in stress being relieved, skin resistance being reduced and likewise the treatment success being improved.

When the above is previously fixed, the invention relates to a system for locally activating the human eyes and the brain for re-organizing neural networks in order to strengthen residual vision and to improve blood circulation in cases of existing visual field defects. In this respect, a pulse current treatment, in particular a non-invasive alternating current treatment is employed.

The system consists of an applicator for guiding the flow of current to the eye and brain, and for exciting the blood circulation and activating nerve cells, in particular retinal ganglion cells.

The system further comprises a pulse generator for generating electric stimulation signals, and a data processing and control unit for providing patient-specific stimulation signal sequences.

The applicator has at least two electrodes which can be brought into contact with the head of the subject in the manner that will still be explained.

According to the invention, replaceable electrodes are fixed to the applicator such that the electrodes rest to the right and the left of the eye in the region of the temple of the patient's head, i.e. in the so-called F7-F8 region.

Furthermore, the applicator has at least one assembly for non-invasively determining the circulation of the skin and the brain and for determining the oxygen saturation, in particular on the basis of fNIR spectroscopy.

A NIR emitter and the at least one associated NIR detector are positioned at a position spaced from the stimulation electrodes on the patient's head and separately from the stimulation electrodes.

The NIR spectroscopy data is detected in breaks or at the end of stimulation signal sequences so as to determine the temporal duration of a persisting improved blood circulation and/or oxygen saturation so that consequently an updated operating of the data processing and control unit may take place via the system according to the invention.

In a further development of the invention, the applicator is individually adaptable to the patient's head shape. For this purpose, adjusting means known as such are formed with respect to being fixed to the patient's forehead and rear head regions.

In a configuration of the invention, the applicator is configured as a ring-shaped or crown-shaped structure that can be brought into contact with the head, wherein a nasal bridge support and/or an ear support and/or a rear head support are/is provided.

Furthermore, a receptacle for electronic components or weight compensation may be provided in the rear head region. The electronic components here may comprise a battery or an accumulator so that the applicator can be used for supplying current free from external wirings.

In a configuration of the invention, the stimulation electrodes are formed as dry pad electrodes or wet pad electrodes.

In a wet pad electrode, an electrolyte may be used as the wet dissolution so as to reduce the contact resistance between the respective conductive component in the electrode and the surface of the patient's skin. The lower the contact resistance, the lower the current for the pulse sequence can be selected, and an unpleasant effect in the meaning of a typical tingling in case of experienced current flow will not occur. On the applicator, fixing points for attaching, in particular for clipping on further electrodes may be provided enabling current application, in particular alternating current application also in the region below the patient's eyes, when this is advantageous from therapeutical points of view.

On or in the applicator, at least one interface is formed for wired or wireless data transmission.

In this way, the applicator can exchange information with a superordinate system via a so-called air interface, register the course of the treatment duration and the treatment success, and can make available or transmit this data to the treating physician for evaluation and further optimization of the treatment.

In a particular configuration of the invention, sound generating means, in particular formed as earphones or headphones are provided on the applicator, so as to guide the patient by information during the treatment, in particular for handling the applicator and/or to relax him acoustically.

For self-sufficient operation, the applicator comprises both the pulse generator, in particular the alternating current pulse generator, and the data processing and control unit together with the current supply, wherein the treatment process and/or the stimulation signal sequence is/are realizable by a computer program product. In this respect, the applicator thus has all the technical means that are necessary for the use and treatment. Accordingly, it is no longer obligatory to provide a separate pulse generating unit which stands besides of the patient either in a wired manner or has to be carried along by the patient, such as it is realized in the known state of the art by devices which are fixed on the belt or carried in the pocket of the patient, for example.

On or in the applicator, an electrolyte reservoir may be provided for wetting the electrodes. Hereby, the patient obtains the possibility to slightly humidify the electrodes himself when the electrodes start to dehydrate. Optionally, the delivery of the electrolyte may also be automatically controlled by a suitable sensor via tubes communicating with the electrode holders.

In a configuration of the invention, the applicator and/or the holders for receiving the electrodes consist of a deformable plastic material. Due to that, there is the possibility to adapt the applicator individually to certain head shapes, in particular in the patient's forehead region, nose region or neck region, and to thereby perform an actual individualization for the patient concerned.

The holders and/or the stimulation electrodes may consist of a conductive plastic material, so that the construction of the applicator is simplified and the current supply or the transmission of the stimulation pulse sequences can be realized via such a conductive material.

It is according to the invention that a bag or a similar receptacle for replacement electrodes is present on the applicator. When an exchangeable electrode gets lost, the treatment cannot be continued, which is in particular then advantageous when the patient to be treated is not in the proximity of the medical surgery usually attending him.

In particular for hospitalized or clinical applications, the applicator may be formed to be combinable for combination with an EEG electrode cap known as such.

As already indicated, the applicator may have a unit for determining the contact resistance between the stimulation electrodes and the patient's skin surface in order to shut off the pulse generator or to reduce the current flow in case of abnormal contact resistances that are too high.

It has been shown that the system according to the invention for locally activating the human eye and the brain may also be used for strengthening the visual performance, in particular for activating nerve cells in the human eye and brain for such persons or test subjects which must execute partially complicated activities under extreme gravitational and/or environmental conditions, such as it is the case, for example, within pilots, astronauts, but also deep-sea divers.

By treating these persons prior to, during and/or after their employment under the depicted extreme conditions, the visual performance is still preserved and enables a concentrated and safer work.

In configuring the invention, there is the possibility to form or adapt the presented applicator such that it may be integrated into a special equipment for the persons mentioned above. Here, the matter is in particular to integrate the applicator in a helmet of a pilot, astronaut or deep-sea diver.

BRIEF DESCRIPTION OF THE DRAWINGS

The invention will be explained in more detail below by means of an exemplary embodiment and with the help of Figures.

Shown are in.

DETAILED DESCRIPTION

Figure 1:
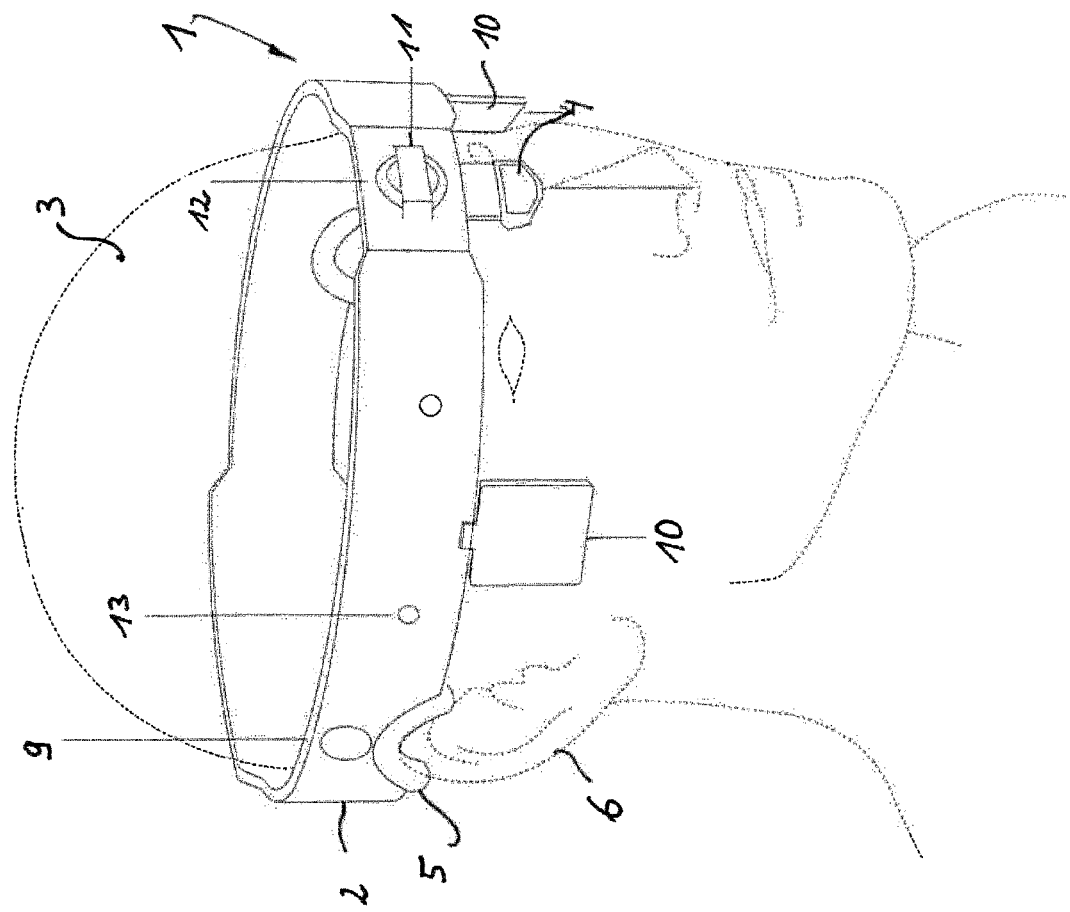
FIG. 1 an exemplary applicator in a front view mounted on the head of a person.
Figure 2:
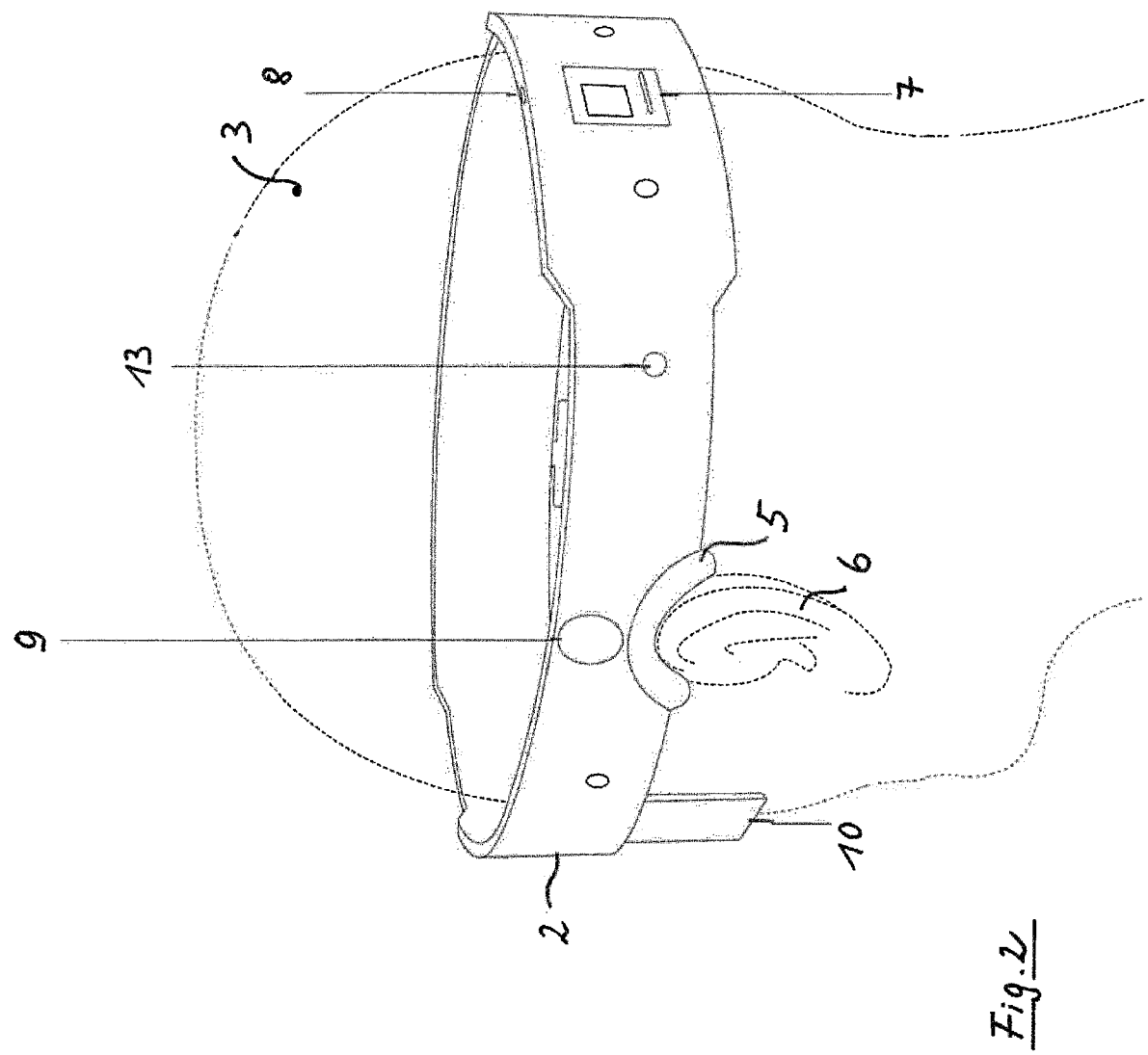
FIG. 2 the applicator in a back view with a view to the person's rear head.

The applicator 1 according to FIGS. 1 and 2 consists of a base body 2 of an at least partially elastic material and is individually adaptable to the head shape of the suggested person 3.

The base body 2 is realized as a ring-shaped or crown-shaped structure that can be mounted on the person's 3 head, wherein a nasal bridge support 4 is present comprising an adjustment option for adapting to anatomical conditions.

Furthermore, the base body 2 is in connection with ear supports 5 for the person's 3 left and right ear 6.

In the rear head region, the base body 2 is provided with a receptacle for electronic components.

This may be a memory unit 7, on the one hand, which comprises stimulation programs. Further preferred, a pulse generator may be accommodated or mounted in this rear head region for generating electric stimulation signals, together with a control unit for providing patient-specific stimulation signal sequences.

Via an interface 8 formed as an USB port, for example, data transmission but also charging of secondary cells 9 may be performed for the purpose of supplying the necessary electric or electronic components with current.

Such a secondary cell 9 may be, for example, a replaceable lithium battery which is accommodated in a respective recess in the base body 2.

Stimulation electrodes 10 are attached on the base body 2 to be replaceable and are arranged such as to lie or rest to the right and the left of the eye in the region of the temple of the suggested head of the patient.

In the front region of the base body 2, an adjustment device 12 is present which may be provided with a labeling field 11 so as to create a space for a company logo, handling instructions or else for attaching a user name or a user identification.

Sensors 13 may be mounted to or embedded into the base body 2 for non-invasively determining the circulation of the skin and the brain and for determining the oxygen saturation. These sensors are spaced apart from the stimulation electrodes 10.

The invention claimed is:

1. A system for locally activating nerve cells in a human eye and a human brain of a patient by means of a non-invasive pulse treatment in order to strengthen residual vision in cases of visual field defects, the system comprising:
    an applicator for guiding a flow of current to the eye and/or brain and to excite circulation and activate the nerve cells,
    a pulse generator for generating electric stimulation signals,
    a memory in which patient-specific stimulation signal sequences are stored,
    a data processor, the data processor being in electrical communication with the memory, a pulse generator controller, the pulse generator controller being in electrical communication with the data processor and the pulse generator, the pulse generator controller being configured to provide the patient-specific stimulation signal sequences to the pulse generator, and
    a unit for determining contact resistance between the stimulation electrodes and a skin surface of the patient in order to shut off the pulse generator, the unit having electronic circuitry that is in electrical communication with the stimulation electrodes,
    wherein the applicator has at least two stimulation electrodes which are configured to be placed in contact with a head of the patient,
    wherein
    the stimulation electrodes are fixed to the applicator and configured to be placed in contact with or rest against a temple region of the patient's head to the right and to the left of an eye of the patient.

2. The system according to claim 1,
    characterized in that
    the applicator is individually adaptable to a shape of the patient's head and adjusting means are formed with respect to being fixed to forehead and rear head regions of the patient.

3. The system according to claim 1,
    characterized in that
    the applicator is formed as a ring-shaped or crown-shaped structure that can be mounted on the head, wherein a nasal bridge support and/or an ear support and/or a rear head support and a receptacle for electronic components und for weight compensation in the rear head region are provided.

4. The system according to claim 3,
    characterized in that
    the electronic components have a current supply.

5. The system according to claim 4, wherein the current supply is a battery or an accumulator.

6. The system according to claim 1,
characterized in that
the stimulation electrodes are formed as dry pad electrodes or wet pad electrodes.

7. The system according to claim 1,
characterized in that
on the applicator, fixing points for attaching further electrodes are provided enabling alternating current application in the region below the patient's eyes.

8. The system according to claim 1,
characterized in that
on or in the applicator, an interface for wired or wireless data transmission is formed.

9. The system according to claim 1,
characterized in that
sound generating means are provided on the applicator, so as to guide the patient by information during the treatment and/or to relax him acoustically.

10. The system according to claim 1,
characterized in that
the pulse generator is an alternating current pulse generator which generates alternating current pulses, and for self-sufficient operation, the applicator comprises each of the alternating current pulse generator, the data processor and the pulse generator controller together with a current supply, wherein the treatment process and/or the stimulation signal sequence is/are realizable by a computer program product.

11. The system according to claim 1,
characterized in that
on or in the applicator, a moisture reservoir is provided for wetting the stimulation electrodes.

12. The system according to claim 1,
characterized in that
the applicator and/or holders for receiving the stimulation electrodes are formed of a deformable plastic material.

13. The system according to claim 1,
characterized in that
the holders and/or the stimulation electrodes are formed of a conductive plastic material.

14. The system according to claim 1,
characterized in that
a bag for receiving stimulation electrodes is present on the applicator.

15. The system according to claim 1,
characterized in that
the applicator is formed to be combinable for combination with an EEG electrode cap known as such.

16. The system according to claim 1,
characterized in that
the applicator has at least one assembly for non-invasively determining circulation of the skin and the brain and for determining oxygen saturation, wherein an NIR emitter and at least one associated NIR detector are positionable at a position spaced from the stimulation electrodes on the patient's head and separately from the stimulation electrodes, and NIR spectroscopy data is detected in breaks or at an end of stimulation signal sequences so as to determine a temporal duration of a persisting improved blood circulation and/or oxygen saturation so that consequently an updated operating of the data processor and the pulse generator controller may be realized.

17. The system according to claim 1,
characterized in that
the position of the stimulation electrodes corresponds to an F7-F8 arrangement according to the nomenclature of the EEG 10-20 system.

18. The system according to claim 1, wherein the nerve cells in the human eye and the human brain are activated by means of a non-invasive alternating current pulse treatment (tASC).

19. The system according to claim 1, wherein the nerve cells are retinal ganglion cells.

20. The system according to claim 1, wherein the stimulation electrodes are replaceable.

21. The system according to claim 1,
characterized in that
on the applicator, fixing points for clipping on further electrodes are provided enabling alternating current application also in a region below the patient's eyes.

22. The system according to claim 1,
characterized in that
sound generating means formed as earphones or headphones are provided on the applicator, so as to guide the patient by information during the treatment and/or to relax him acoustically.

23. The system according to claim 1,
characterized in that
the applicator has at least one assembly for non-invasively determining circulation of the skin and the brain and for determining oxygen saturation on the basis of fNIR spectroscopy,
wherein an NIR emitter and at least one associated NIR detector are positionable at a position spaced from the stimulation electrodes on the patient's head and separately from the stimulation electrodes, and NIR spectroscopy data is detected in breaks or at an end of stimulation signal sequences so as to determine a temporal duration of a persisting improved blood circulation and/or oxygen saturation so that consequently an updated operating of the data processor and the pulse generator controller may be realized.

* * * * *